United States Patent
Kendall

(10) Patent No.: US 6,963,632 B2
(45) Date of Patent: Nov. 8, 2005

(54) OPTIMIZED X-RAY TUBE COOLING DEVICE

(75) Inventor: Charles B. Kendall, Brookfield, WI (US)

(73) Assignee: GE Medical Systems Global Technology Company, LLC, Waukesha, WI (US)

(*) Notice: Subject to any disclaimer, the term of this patent is extended or adjusted under 35 U.S.C. 154(b) by 76 days.

(21) Appl. No.: 10/448,550

(22) Filed: May 30, 2003

(65) Prior Publication Data

US 2004/0240619 A1 Dec. 2, 2004

Related U.S. Application Data

(60) Provisional application No. 60/472,659, filed on May 22, 2003.

(51) Int. Cl.[7] ............................................. H01J 35/10
(52) U.S. Cl. .................................... 378/141; 378/199
(58) Field of Search .......................... 378/4, 130, 141, 378/199, 200, 204; 165/104.11, 110, 164

(56) References Cited

U.S. PATENT DOCUMENTS

| | | | | |
|---|---|---|---|---|
| 5,610,968 A | * | 3/1997 | Deucher et al. | 378/199 |
| 5,956,383 A | * | 9/1999 | Kendall | 378/199 |
| 6,491,428 B1 | | 12/2002 | Takanashi | 378/200 |
| D486,898 S | * | 2/2004 | Kendall | D23/323 |

* cited by examiner

Primary Examiner—Edward J. Glick
Assistant Examiner—Courtney Thomas
(74) Attorney, Agent, or Firm—Peter J. Vogel; Artz & Artz, P.C.

(57) ABSTRACT

A cooling system to cool the x-ray tube of a CT imaging system. The heat exchanger has a curved sector shape which provides a larger surface area for heat dissipation within the cover of the gantry. The axis of the cooling fans is preferably parallel to the rotational axis of the gantry.

31 Claims, 4 Drawing Sheets

OPTIMIZED X-RAY TUBE COOLING DEVICE

CROSS-REFERENCE TO RELATED APPLICATIONS

This case is related to the subject matter as set forth in Provisional Patent Application Ser. No. 60/472,659 filed on May 22, 2003.

TECHNICAL FIELD

The present invention relates generally to CT imaging systems, and more particularly to imaging systems that use fans and heat exchangers as part of the cooling systems.

BACKGROUND OF THE INVENTION

Computed tomography (CT) imaging systems are in wide use today. The CT systems include a gantry that has a frame which rotates in order to create a 360° image. The gantry frame includes an x-ray tube as well as a cooling system to control the temperature of the x-ray tube. The cooling system typically employs a liquid-to-air heat exchanger to remove heat from the x-ray tube during operation. The cooling system also typically includes one or more fans that are used to draw air through the heat exchanger and exhaust heated air from the gantry.

The size and surface area of the heat exchanger required in a particular application is partly a function of the power to be dissipated, and the temperature of the ambient air sent through the heat exchanger. On high power CT systems, the ambient air temperature in combination with the higher power requirements often makes the packaging difficult for large heat exchangers.

Also, when larger heat exchangers have been utilized, the axis of rotation of the fans have not been parallel to the axis of rotation of the gantry, which leads to geoscopic loading. The fans are more reliable when their rotation axis is parallel to the gantry axis.

It would, therefore, be desirable to provide a heat exchanger with a larger surface area for cooling and still be confined in the space requirements of the gantry. It also would be desirable to have a larger area heat exchanger and maintain the fan axis of rotation parallel to the gantry axis of rotation.

SUMMARY OF THE INVENTION

It is an object of the present invention to provide an improved heat exchanger for the cooling system of a CT imaging system. It is another object of the present invention to provide a package for a heat exchanger that presents a larger surface area to dissipate heat and still maintain an axial air flow direction.

It is a still additional object of the present invention to provide a cooling system for a CT imaging system that improves the thermal performance of the CT system. It is still another object of the present invention to provide a cooling system that allows for greater heat transfer surface area of the heat exchanger and still allow the heat exchanger to be easily packaged in the gantry.

These and other objects of the present invention are accomplished by the method apparatus and system set forth in the accompanying specification, drawings, and claims. In addition, the present invention has many benefits and advantages over known apparatus, methods and systems which are used to cool x-ray tubes in CT imaging systems.

In accordance with the present invention, the heat exchanger for the cooling system is shaped and provided to fit within as much of the allowable space as possible in the gantry. In this regard, gantrys typically have a tight fitting cover structure that generally has an annulus or "doughnut" shape. The inventive heat exchanger is preferably shaped as a sector of an annulus with the curvature matching the rotating envelope of the CT gantry. This shape presents the largest surface area possible within the gantry to dissipate heat.

The heat exchanger is also positioned to allow air flow through it in a direction parallel to the axis of the gantry. This allows positioning of the cooling fans such that their axes of rotation is also parallel to the gantry axis. This eliminates gyroscopic loading on the fan shaft when the fan axis and gantry axis are not in parallel.

Other aspects and advantages of the present invention will become apparent upon the following detailed description and appended claims, and upon reference to the accompanying drawings.

BRIEF DESCRIPTION OF THE DRAWINGS

For a more complete understanding of the invention, reference can be made to the embodiments illustrated in greater detail in the accompanying drawings and described below by way of examples.

DESCRIPTION OF THE PREFERRED EMBODIMENT(S)

Figure 1:
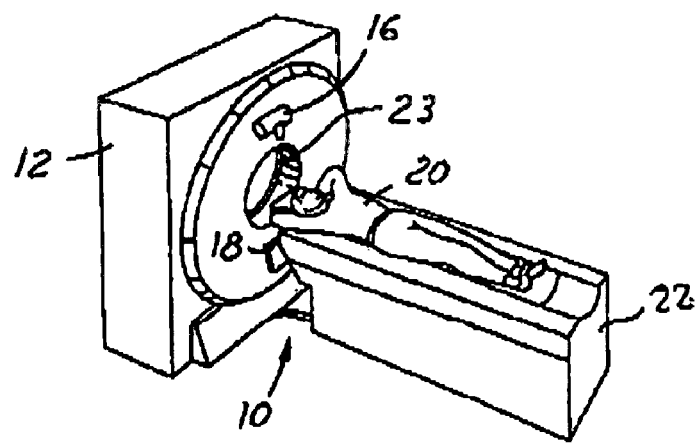
FIG. 1 is a schematic illustration of a CT system illustrating its general components.

In each of the following figures, the same reference numerals are used to refer to the same components. Also, while the present inventions are described with respect to apparatuses, systems, and methods of improving cooling systems of computed tomography (CT) imaging systems, the present inventions are capable of being adapted for various purposes are not limited strictly to CT systems. For example, the present inventions can be utilized in MRI systems, radio therapy systems, other x-ray imaging systems, ultrasound systems, nuclear imaging systems, magnetic resonant spectroscopy systems, and other applications and systems known in the art.

Also, although the present invention is described as being used in connection with x-ray tubes for CT imaging systems, the present invention can be used in conjunction with other imaging tubes, including vascular tubes.

In the following description, various operating parameters and components are described for preferred embodiments of the present invention. The specific parameters and embodiments are included only as examples and are not meant to be limiting.

Referring now to FIG. 1, a schematic illustration of a conventional computed tomography (CT) system is disclosed and referred to generally by the reference numeral 10. The imaging system 10 includes a gantry 12 that has an x-ray imaging tube 16. The imaging tube 16 projects a beam of x-rays toward a detector array 18.

When the CT imaging system is utilized, a patient 20 positioned on a movable slider tray mechanism 22 is positioned in the central bore 23. X-rays from the imaging tube 16 pass through the patient within the bore 23 and are detected by the detector array 18 and used to create a CT image or a construction.

Figure 2:
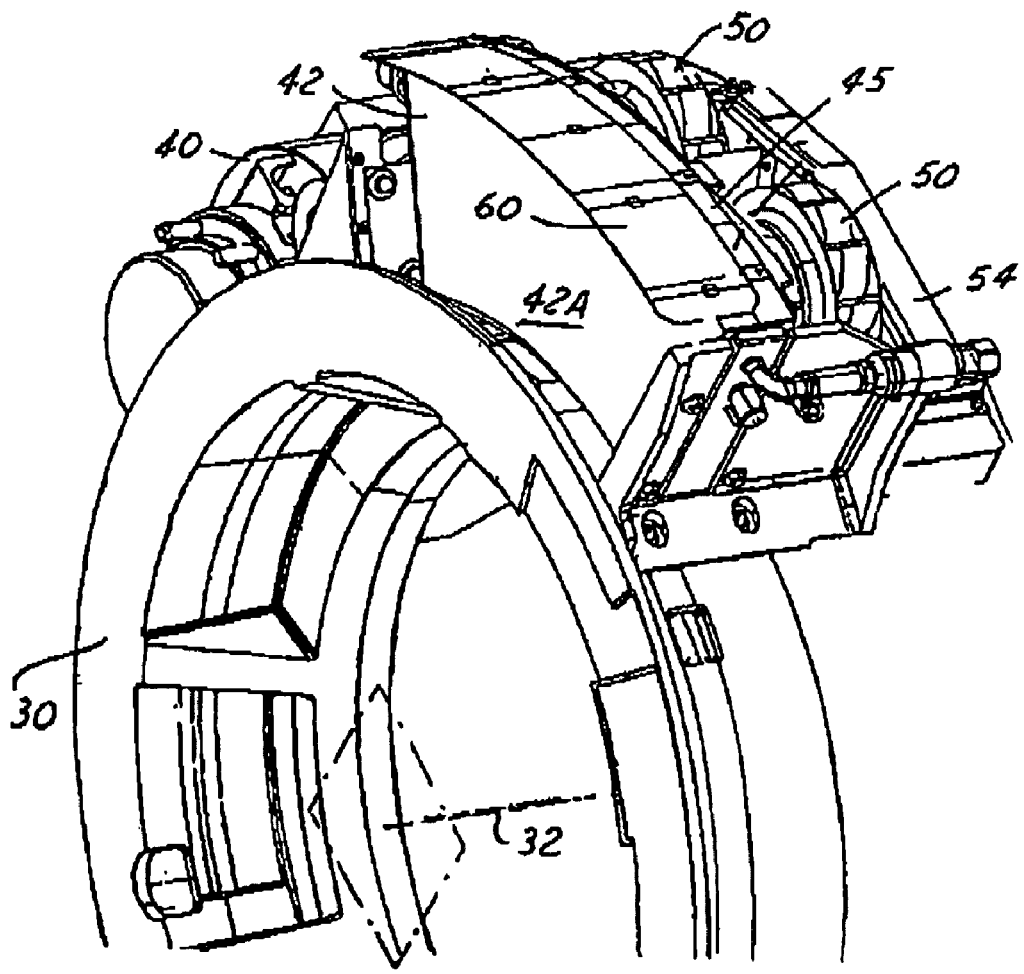
FIG. 2 illustrates a portion of the gantry system depicting several of its internal components in accordance with the present invention.

FIG. 2 illustrates a number of the inner components of the gantry member 12. The gantry has an outer cover or structure 13 and a rotating inner annular frame member 30 which rotates about a gantry axis 32. The frame member 30 has a number of components attached to it and which rotate with it. These components include an x-ray tube 40, a heat exchanger 42, one or more fan members 50, two of which are shown in FIG. 2, and a fan mounting bracket 54. The cover 13 has at least one surface which is positioned relatively close to the cooling system components as they are rotated inside the cover. Typically, the clearance is about 0.50 inches to about 6.0 inches.

The CT system illustrated is simplified to highlight the aspects of the present invention. Those skilled in the art will recognize various other components that need to be present and included in such systems. For example, CT system 10 also includes a controller which is preferably micro-processor based. The controller is designed to control the operation of the cooling system for the x-ray tube 40.

The cooling system includes as its principal components, the heat exchanger 42 and the fans 50. In this regard, the heat exchanger 42 is preferably an oil-to-air heat exchanger and is also commonly called a "oil cooler." Liquid-to-air types of heat exchangers are typically used in x-ray systems. Also, in the embodiment shown in the drawings, the fans 50 are integrally coupled to the heat exchanger 42. Persons skilled in the art will recognize that one or more fans may be separate components placed adjacent to the heat exchanger.

The cooling fans 50 are designed to help move air through the heat exchanger to cool the liquid circulating in the heat exchanger and ultimately the x-ray tube 40. The controller (not shown) is operably coupled to the fans to control their speed and thus control the amount of cooling in the system. In this regard, the speed of the fan preferably varies over the operating temperature range of the x-ray tube. When a predetermined temperature is reached, such as 100° F., the fan speed is elevated to maintain a maximum fan speed. The maximum fan speed could be, for example, 2900 rpm. Also, the output of the controller and thus the operation of the fan does not necessarily have to be linear.

An air deflector 60 is also shown in FIG. 2. An air deflector (a/k/a "visor") is attached to the heat exchanger 42 and extends over the front face 42A thereof. In this regard, air passing through the heat exchanger is introduced into the exchanger through front surface 42A and thus is pulled through the heat exchanger by the fans 50.

Figure 3:
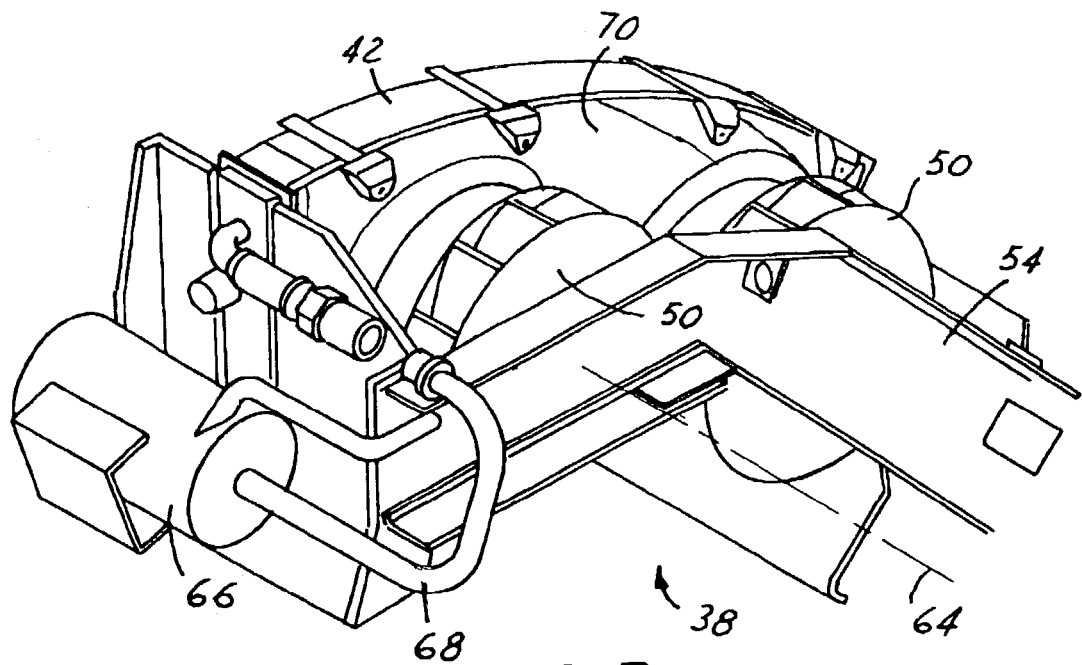
FIG. 3 illustrates an embodiment of the present invention.

Another embodiment of the present invention is shown in FIG. 3. As shown, the fan axis 64 is parallel to the gantry axis 32. This is the preferred orientation of the air flow and fan rotation in accordance with the present invention. In this manner, the fans 50 which are associated with the heat exchanger 42, are oriented with the rotational axis parallel to their rotational axis of the gantry. This eliminates gyroscopic loading on the fan shaft when the fan axis and gantry axis are not in parallel.

The cooling system is generally referred to by reference numeral 38 in FIG. 3 and also includes a pump 66 and a shroud member 70. The pump 66 is used to circulate cooling oil through conduit 68 into and out of the heat exchanger 42. The shroud 70 is used to direct air passing through the heat exchanger through the fans 50.

Figure 4:
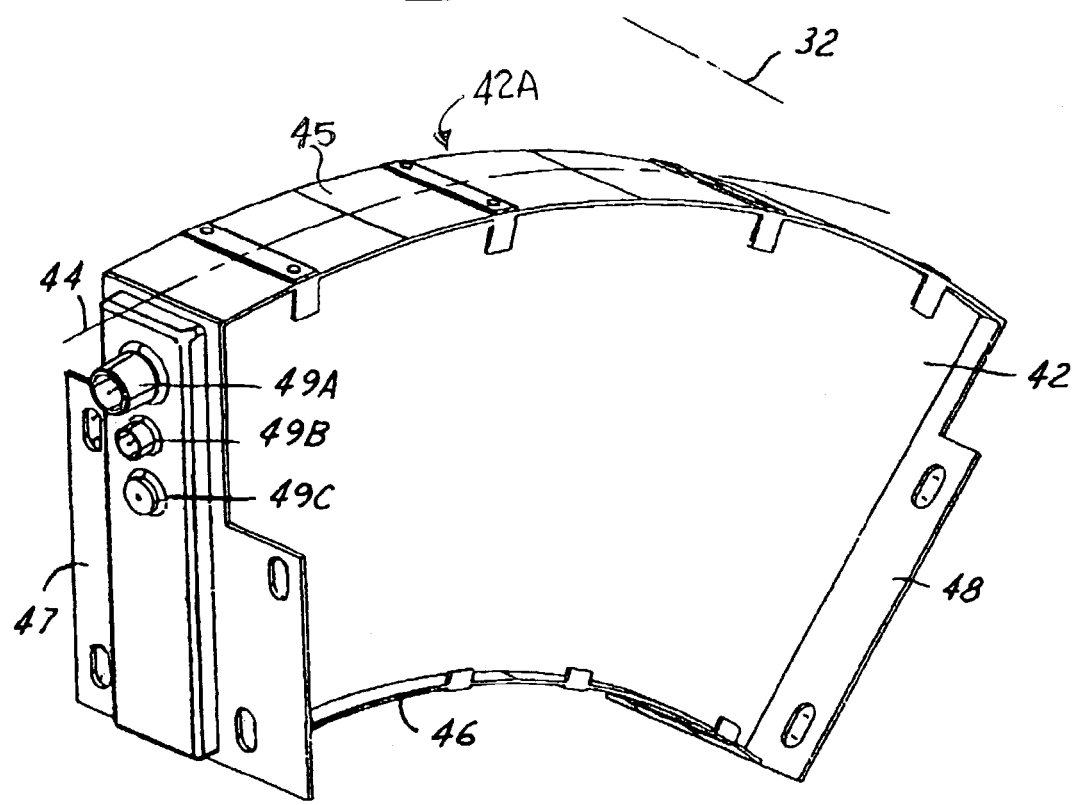
FIGS. 4, 5, and 6 are various views of a preferred heat exchanger in accordance with an embodiment of the present invention.
Figure 5:
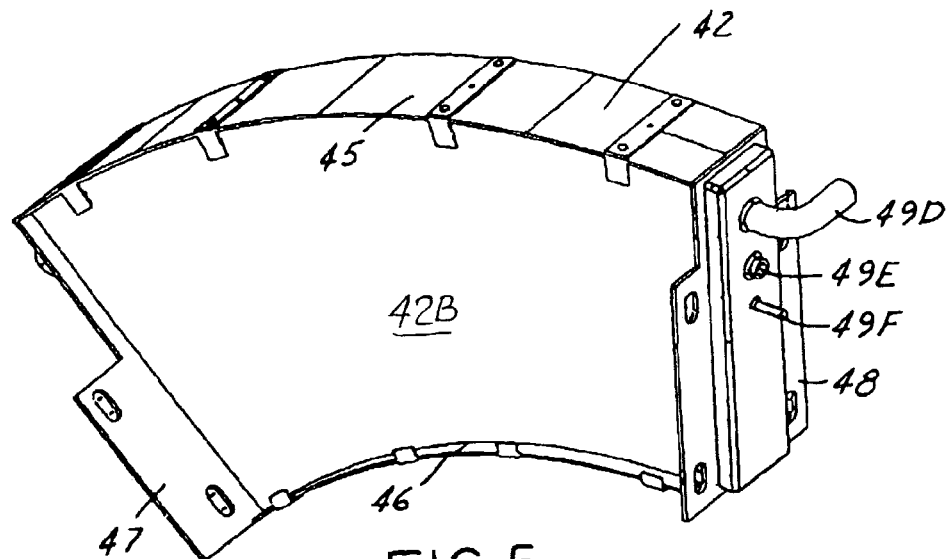
Figure 6:
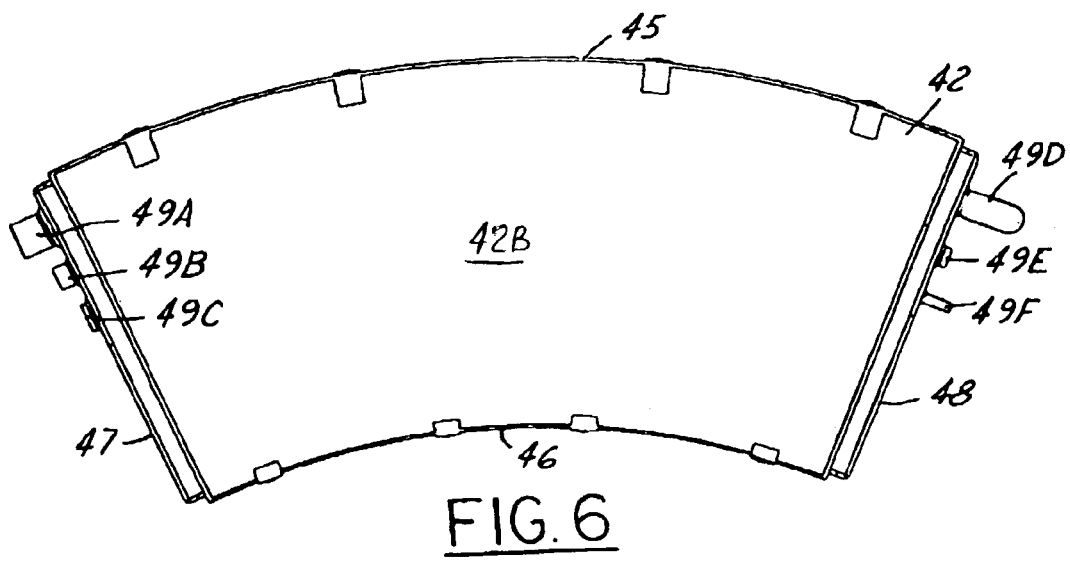

The preferred shape of the heat exchanger 42 in accordance with the present invention is shown in FIGS. 4, 5, and 6. The heat exchanger is formed in the shape of a sector of an annulus and has a curvature 44 that matches the rotating envelope of the CT gantry. The curved shape of the heat exchanger presents the largest surface area which can be utilized to dissipate heat from the gantry and CT imaging system within the gantry cover. There is a limited amount of space available in the tight fitting cover of the rotating gantry in conventional CT imaging systems. Conventional heat exchangers are typically rectangular in shape and are limited in size in order to allow the heat exchanger to fit within the available space.

It is also important with the present invention to position the heat exchanger in the manner and position shown in FIG. 2, i.e. with the substantially planar side surfaces 42A and 42B positioned to allow the fan to rotate about axes parallel to the gantry axis 32. The maintenance of axial air flow through the heat exchanger and through the gantry is preferred.

In the heat exchanger shown in FIGS. 4–6, the device has supporting and/or mounting members on the four perimeter surfaces. For example, curved brackets 45 and 46 are positioned on the upper and lower perimeter surfaces, respectively, of the heat exchanger 42, while mounting brackets 47 and 48 are positioned on the two end perimeter surfaces. The end mounting brackets 47 and 48 also contain various hardware for inflow and outflow of the oil through the coils inside the heat exchanger (not shown). This hardware is referred to generally by the reference numerals 49A–49F.

Figure 7:
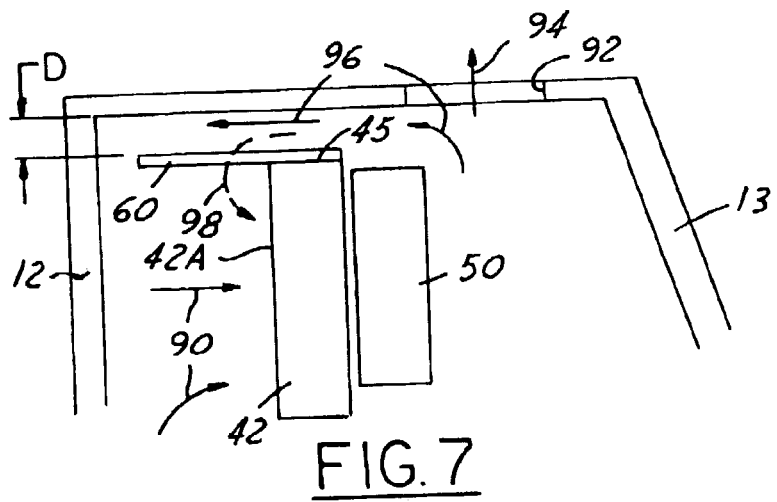
FIG. 7 is a schematic diagram illustrating the use of a deflector member with a heat exchanger.

FIG. 7 schematically illustrates an air deflector 60 which can be utilized with the present invention in order to affect the air flow inside the gantry and prevent recirculation of heated air. As indicated, the air deflector or visor 60 is attached or connected to the heat exchanger 42. Cooler inlet air represented by arrow 90 is pulled into and through the heat exchanger 42 by the fan 50, which is positioned immediately behind the heat exchanger. Most of the air which passes through the fan 50 and the gantry 12 is exhausted through air vent 92, as represented by arrow 94.

However, as shown in FIG. 7, a portion of the heated air is often recirculated inside the cover 13 of the gantry in a direction toward the front surface 42A of the heat exchanger 42. This recirculated air is indicated by arrows 96. Without the air deflector 60 in place, the recirculated air, which is at an elevated temperature, follows the path of the arrow 98 which is shown in dotted lines and passes back through the heat exchanger and fan.

Cooling air drawn into the heat exchanger is normally supplied by air that is already present in the gantry during operation. The cooling air temperature increases as it absorbs heat from the tube oil flowing through the heat exchanger 42. The heated air is preferably exhausted from the heat exchanger through air vent 92. When the gantry is brought to a stationary position, the heated exit air is directed to the air vents 92 on the gantry cover or structure 13. However, due to the close spacing between the gantry cover and the rotating cooling system components, some of the heated air is retained within the cover 13 and is reingested into the heat exchanger. When this happens, the x-ray tube oil can stabilize at an elevated temperature and reduce the thermal performance of the system. The use of an air deflector 60 reduces the ingestion of previously heated air and forces the air going into the heat exchanger to come from the inboard regions of the gantry. The x-ray tube oil thus runs at a lower nominal temperature resulting in increased thermal performance of the CT system.

Figure 8:
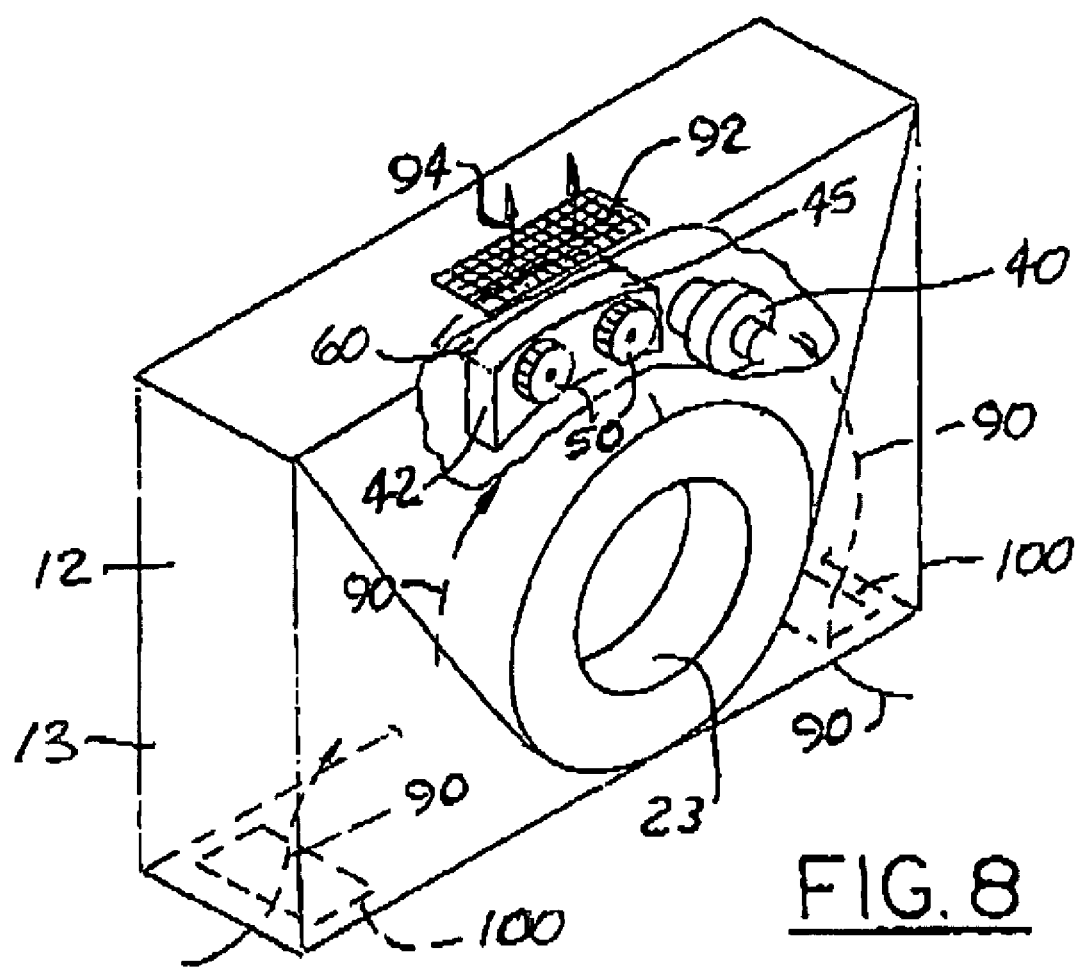
FIG. 8 is a schematic diagram illustrating an embodiment of the inventive heat exchanger with a deflector member.

FIG. 8 is another schematic view of a gantry and cooling system in accordance with the present invention. As illustrated, cool inlet air 90 is drawn up through the gantry 12 through air vents 100 positioned in the lower portions of the cover structure 13. The cooled inlet air is then directed toward the front surface of the heat exchanger 42 as schematically shown in FIG. 7. The heat exchanger 42 has a curved (sector) shape and is positioned with the pair of fans 50 in order to allow air flow in an axial direction relative to the gantry axis of rotation. An air deflector 60 can be added to prevent recirculation of heated air.

While particular embodiments of the invention have been shown and described, numerous variations and alternative embodiments will occur to those skilled in the arm. Accordingly, it is intended that the invention be limited only in terms of the appended claims.

What is claimed is:

1. A heat exchanger for cooling an x-ray tube, said heat exchanger comprising:
   a body; and
   a containment portion within said body for separating a first coolant from a second coolant, said body having a shape substantially as a sector of an annulus, said sector of an annulus defining an axial direction, said axial direction substantially aligned with the axial orientation of a medical imaging device, wherein said second coolant may axially pass through said body.

2. The heat exchanger as described in claim 1 wherein said body has an upper perimeter surface, a lower perimeter surface, a first end perimeter surface and a second end perimeter surface, said upper perimeter surface having a curved configuration, whereby said second coolant is bounded by said perimeter surfaces.

3. The heat exchanger as described in claim 2 wherein both of said upper perimeter surface and said lower perimeter surface have curved configurations.

4. The heat exchanger as described in claim 2 wherein said curved configuration has a constant radius of curvature.

5. The heat exchanger as described in claim 2 further comprising a deflector wherein said deflector extends axially from said upper perimeter surface.

6. The heat exchanger as described in claim 2 wherein at least one of said first and second end perimeter surfaces has a mounting bracket thereon, and wherein at least one of said first and second end perimeter surfaces has at least one liquid fixture thereon.

7. The heat exchanger as described in claim 6 wherein each of said first and second end perimeter surfaces has a mounting bracket thereon and wherein each of said first and second end perimeter surfaces has at least one liquid fixture thereon.

8. The heat exchanger as described in claim 1 further comprising at least one fan member in operative association with said heat exchanger, said heat exchanger having at least one substantially planar side surface and said fan member having an axis of rotation substantially perpendicular to said planar side surface.

9. The heat exchanger as described in claim 8 wherein two of said fan members are provided, each of said fan members having an axis of rotation substantially perpendicular to said planar side surface.

10. A computed tomography (CT) imaging system comprising:
    a gantry member, said gantry member having a rotating frame member and an axial direction;
    an x-ray tube positioned on said frame member;
    a heat exchanger positioned on said frame member adjacent said x-ray tube and adapted to cool said x-ray tube; and
    at least one fan member positioned adjacent said heat exchanger and adapted to flow air through said heat exchanger in said axial direction;
    said heat exchanger having a configuration which is substantially a section of an annulus.

11. The computed tomography (CT) imaging system as described in claim 10 further comprising a shroud positioned between said heat exchanger and said at least one fan member.

12. The computer tomography (CT) imaging system as described in claim 10 wherein said gantry member has a first axis of rotation and said fan member has a second axis of rotation, said first and second axes of rotation being substantially parallel to one another.

13. The computer tomography (CT) imaging system as described in claim 10 wherein said heat exchanger has an upper perimeter surface, a lower perimeter surface, a first end perimeter surface and a second end perimeter surface, said upper perimeter surface having a curved configuration, wherein the flow of air is bounded by said perimeter surfaces.

14. A computer tomography (CT) imaging system as described in claim 13 wherein each of said upper perimeter surface and said lower perimeter surface has a curved configuration.

15. A computer tomography (CT) imaging system as described in claim 13 wherein said curved configuration has a constant radius of curvature.

16. A computer tomography (CT) imaging system as described in claim 13 further comprising a deflector wherein said deflector extends axially from said upper perimeter surface.

17. The computer tomography (CT) imaging system as described in claim 16 wherein said deflector has a curvature that matches said curved configuration of said upper perimeter surface.

18. A computer tomography (CT) imaging system as described in claim 13 wherein at least one of said first and second end perimeter surfaces has a mounting bracket thereon, and wherein at least one of said first and second end perimeter surfaces has at least one liquid fixture thereon.

19. A computer tomography (CT) imaging system as described in claim 18 wherein each of said first and second end perimeter surfaces has a mounting bracket thereon and wherein each of said first and second end perimeter surfaces has at least one liquid fixture thereon.

20. A computer tomography (CT) imaging system as described in claim 10 wherein said heat exchanger has at least one substantially planar side surface and said fan member has an axis of rotation, and wherein said axis of rotation is substantially perpendicular to said planar side surface.

21. A computer tomography (CT) imaging system as described in claim 20 wherein two of said fan members are provided, each of said fan members having an axis of rotation substantially perpendicular to said planar surface.

22. The computer tomography (CT) imaging system as described in claim 10 wherein said heat exchanger is a liquid-to-air type heat exchanger, wherein said liquid is an oil material.

23. The computer tomography (CT) imaging system as described in claim 10 further comprising a cover member covering said rotating frame member, x-ray tube and heat exchanger, said cover member having at least one surface which is spaced a distance of 0.50 to 6.0 inches from said heat exchanger.

24. A cooling system for an x-ray tube, said cooling system comprising a heat exchanger in fluid communication with at least one fan member, said heat exchanger having a curved upper perimeter surface member, a lower perimeter surface member, two opposite end perimeter members, a deflector and two opposed planar side surfaces, wherein said deflector extends axially from said upper perimeter surface member, whereby fluid is deterred from reentering said heat exchanger after being expelled by said fan member.

25. The cooling system as described in claim 24 wherein said lower perimeter surface member has a curved configuration and said heat exchanger has the shape of a sector of an annulus.

26. The cooling system as described in claim 25 wherein the curvatures of the upper and lower perimeter surface members each have a constant radius of curvature.

27. The cooling system as described in claim 24 wherein said at least fan member has an axis of rotation, said axis of rotation being substantially perpendicular to at least one of said planar side surfaces.

28. The cooling system as described in claim 24 wherein said heat exchanger is a liquid-to-air heat exchanger.

29. The cooling system as described in claim 24 wherein said heat exchanger is an oil-to-air heat exchanger.

30. The cooling system as described in claim 24 wherein two of said fan members are provided in air flow communication with said heat exchanger.

31. The cooling system as described in claim 24 further comprising a shroud member positioned between said heat exchanger and said at least one fan member.

* * * * *